United States Patent [19]

van der Knaap

[11] Plant 4,589

[45] Aug. 26, 1980

[54] CHRYSANTHEMUM NAMED WESTLAND

[75] Inventor: J. C. M. van der Knaap, De Lier, Netherlands

[73] Assignee: Pan-American Plant Company, West Chicago, Ill.

[21] Appl. No.: 13,303

[22] Filed: Feb. 21, 1979

[51] Int. Cl.³ ..... A01H 5/00

[52] U.S. Cl. ..... Plt./80

[58] Field of Search ..... Plt./80

*Primary Examiner*—Robert E. Bagwill

*Attorney, Agent, or Firm*—Chas. W. Rummler

[57] ABSTRACT

A new variety of chrysanthemum intended for glass house culture for cut flower production distinguished by the pink coloration of the quill-shaped ray florets of its uniquely formed medium-sized blooms, its vigorous upright growth habit, and its year around 9-week photoperiodic flowering response.

4 Drawing Figures

BACKGROUND OF THE NEW PLANT

My new chrysanthemum cultivar originated as a seedling which resulted from my crossing of Yellow Augusta with Dark Flamenco as the pollen parent (both unpatented) in 1973 at De Lier, Holland, in the course of my efforts to produce improved chrysanthemums for the commercial market. I propagated this new plant at De Lier, Holland, by means of cuttings from the original plant and through successive generations by vegetative cuttings and determined that its distinctive characteristics hold true from generation to generation and thus appear to be firmly fixed.

This new plant is now being propagated for commercial purposes, by means of vegetative cuttings, at West Chicago, Ill., and at Cortez, Fla., U.S.A.

DESCRIPTION OF THE DRAWINGS

My new chrysanthemum cultivar is illustrated by the accompanying drawings, of which the first sheet is a full color photographic rendition of the full bloom inflorescence appearing on a typical main stem, the color shown being as nearly true as is reasonably possible to obtain by conventional photographic procedures; and the second sheet is a mechanical reproduction of a photoprint of typical leaves of the new plant.

DESCRIPTION OF THE NEW PLANT

The following is a detailed description of my new variety of chrysanthemum based upon observations made at West Chicago, Ill., U.S.A., in the Spring of 1978, with color designations according to The R.H.S. Colour Chart published by The Royal Horticultural Society of London, England.

THE PLANT

Origin: Seedling.

Parentage:

*Seed parent.*—Yellow Augusta (unpatented).

*Pollen parent.*—Dark Flamenco (unpatented).

Classification:

*Botanic.*—*Chrysanthemum morifolium.*

*Commercial.*—Greenhouse plant for cut flowers.

Form: Perennial herbaceous bush.

Height: About 105 to 124 cm.

Growth: Terminal; vigorous, upright and sturdy with good strength.

Branching: Usual under normal conditions.

Foliage:

*Quantity.*—Abundant. 4 leaves per 15 cm. of stem length.

*Leaf size.*—Length — about 8.6 to 15.3 cm. Width — about 4.6 to 8.5 cm.

*Shape.*—Lobed, lanceolate and slightly serrated.

*Surface texture.*—Canescent.

*Color.*—Upper side — 147A. Under side — 147B.

*Venation.*—Pinnate.

*Petioles.*—About 2.4 to 4.7 cm. long.

THE BUD

Form: Globular.

Size:

*Diameter.*—8 to 10 mm.

*Depth.*—6 to 8 mm.

Opening rate: The bud opens slowly.

Color:

*When phyllaries first divide.*—186D.

*When florets begin to unfurl.*—186B and 186C.

Phyllaries: The receptacle bears many involucral bracts on the outer side and the bracts are spear-shaped and upstanding.

*Color.*—Inside — 137A. Outside — 137B.

*Surface texture.*—Pubescent.

Peduncle: Erect and strong.

*Length.*—About 8 to 19 cm.

*Surface texture.*—Pubescent.

THE FLOWER

Response: 9 week.

Recommended flowering: Year around with photoperiod control.

Natural season flowering: October 27 to November 5.

Blooms:

*Flower type.*—Composite and quilled.

*Size.*—Medium. Diameter: About 8 to 9 cm. Depth: About 3.2 to 4.0 cm.

*Borne.*—Singly and comprising a head of many florets borne on a receptacle, the flower peduncle being one of many carried in racemose fashion on a strong, upright main stem.

*Shape.*—Cup-shaped when bloom first opens and becoming hemispherical as the bloom matures.

Florets:

*Number.*—Numerous.

*Form.*—Quill.

*Color.*—Outer florets: Upper side — 73D. Inside of quill — 74D. Disc floret — 180C, 180D.

*Appearance.*—Very slight shine.

Peduncle: Sturdy and upright, 8 to 19 cm. long.

*Color.*—147B.

Persistence: Florets hang on and dry.

Discoloration after full bloom: Moderate fade.

Fragrance: Typical chrysanthemum.

Lasting quality:

*On the plant.*—3 weeks.

*As a cut flower.*—2 to 3 weeks. Recommended for greenhouse culture only.

REPRODUCTIVE ORGANS

Stamens:

*Anthers.*—None present.

Pistils:

*Number.*—One to each ray floret.

*Styles.*—4 to 6 mm. long.

*Stigmas.*—Color — yellow.

Characteristics of ovaries: Inferior, bicarpellate.

The particular distinctions of this new cultivar of chrysanthemum reside particularly in the spidery shape of its blooms with quill-shaped ray florets having a distinctive pink color, the blooms averaging about 8.5 cm. in diameter and the plant having particular usefulness as a cut spray capable of uniform flowering response the year around.

I claim:

1. A new and distinct variety of chrysanthemum plant, substantially as herein shown and described, characterized by its unique quill-shaped ray florets of a light pink color radiating from a reddish disc, and its uniform year-around flowering response under 9-week photoperiodic control.

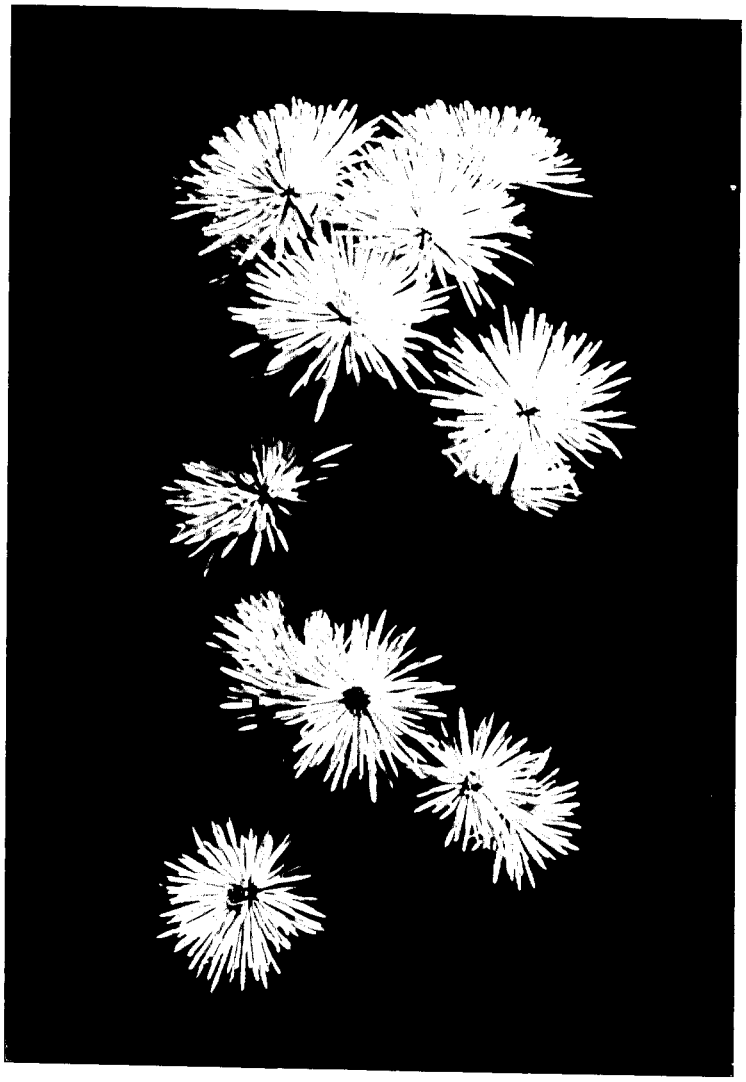

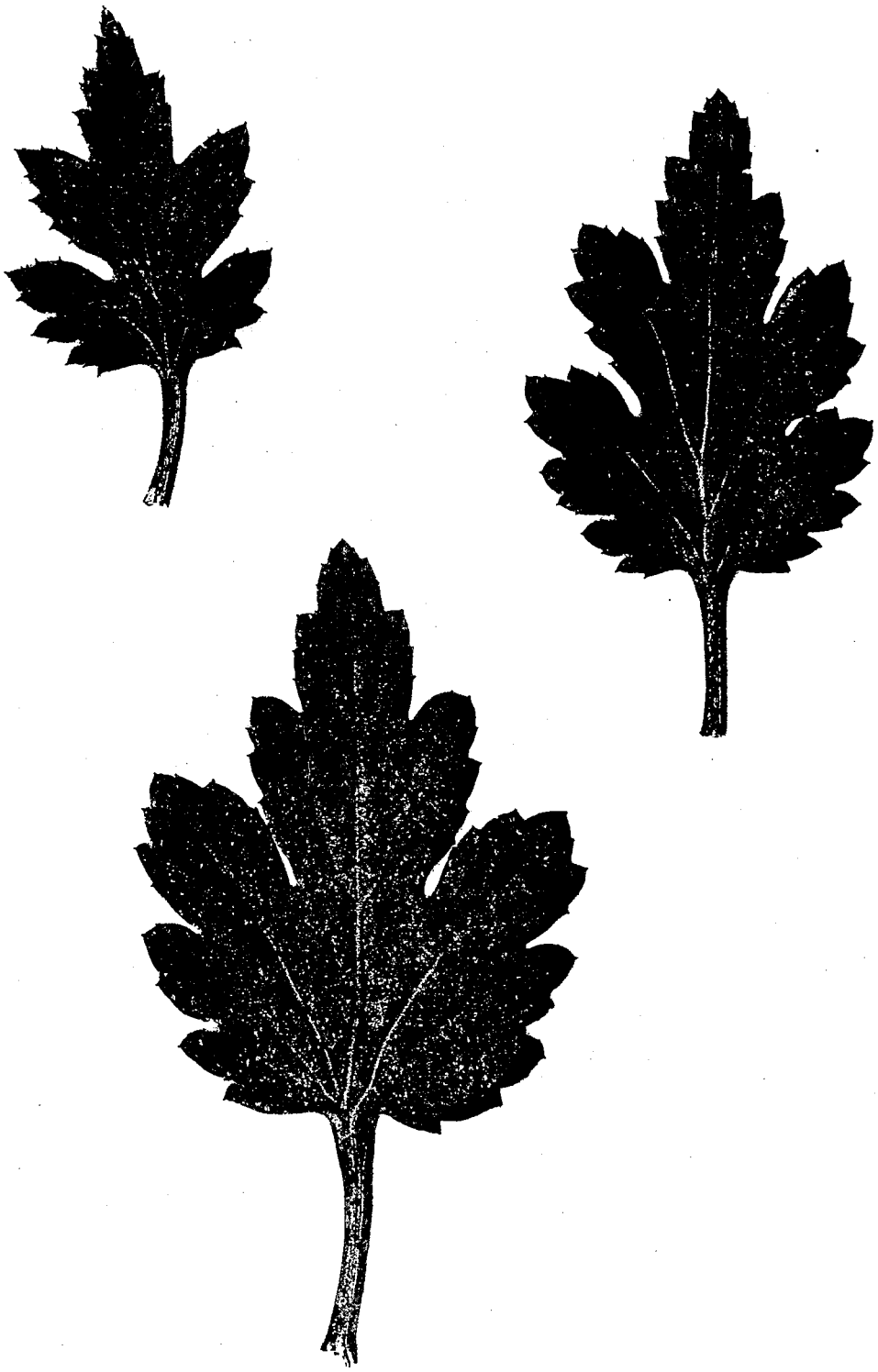

* * * * *